United States Patent [19]

Subramanian

[11] 4,442,041
[45] Apr. 10, 1984

[54] METHOD FOR PREPARATION OF N-PHOSPHONOMETHYLGLYCINE

[75] Inventor: N. Subramanian, Hercules, Calif.

[73] Assignee: Stauffer Chemical Company, Westport, Conn.

[21] Appl. No.: 499,588

[22] Filed: May 31, 1983

Related U.S. Application Data

[63] Continuation-in-part of Ser. No. 393,573, Jun. 30, 1982.

[51] Int. Cl.³ ............................................. C07F 9/38
[52] U.S. Cl. ............................................. 260/502.5 F
[58] Field of Search .................................. 260/502.5 F

[56] References Cited

U.S. PATENT DOCUMENTS

| | | | |
|---|---|---|---|
| 3,842,081 | 10/1974 | Schulze et al. | 562/418 |
| 3,864,369 | 2/1975 | Isa et al. | 562/524 |
| 3,907,652 | 9/1975 | Wagenknecht et al. | 260/502.5 F |
| 3,954,848 | 5/1976 | Franz | 260/502.5 F |
| 3,969,398 | 7/1976 | Herschman | 260/502.5 F |
| 4,067,932 | 1/1978 | Muntz et al. | 260/968 |
| 4,147,719 | 4/1979 | Franz | 260/502.5 F |

FOREIGN PATENT DOCUMENTS

| | | | |
|---|---|---|---|
| 2049697 | 12/1980 | United Kingdom | 260/502.5 F |

*Primary Examiner*—J. E. Evans
*Attorney, Agent, or Firm*—Paul R. Martin

[57] ABSTRACT

A method for the preparation of N-phosphonomethylglycine is disclosed which comprises the steps of:

(1) reacting N-(diethylphoshonomethyl)iminobisethanol in an oxygen free atmosphere with an alkali metal hydroxide selected from the group consisting of sodium hydroxide and potassium hydroxide, in the presence of water as solvent and a catalyst selected from the group consisting of zinc oxide and cadmium oxide at a high temperature and pressure for a sufficient period of time to cause the reaction to go to completion, and (2) acidifying the product formed.

6 Claims, No Drawings

METHOD FOR PREPARATION OF N-PHOSPHONOMETHYLGLYCINE

CROSS REFERENCE TO RELATED APPLICATIONS

This application is a continuation-in-part of U.S. application Ser. No. 393,573, filed June 30, 1982.

BACKGROUND OF THE INVENTION

This invention relates to a novel method for the preparation of N-phosphonomethylglycine, a compound which is a known herbicide and plant growth regulator.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and postemergence herbicides. The pre-emergence herbicides are normally incorporated into the soil prior to the emergence of the weed plants from the soil, and the post-emergence herbicides are normally applied to plant surfaces after emergence of the weeds or other unwanted plants from the soil.

One of the earliest post-emergence herbicides used commercially was 2,4-D (2,4-dichlorophenoxyacetic acid). After a number of years of use of this and similar compounds such as 2,4,5-T (2,4,5-trichlorophenoxy acetic acid), it was found that certain decomposition products of these herbicides were long lasting and were not biodegradable. While there has been some dispute between governmental agencies and commercial interests regarding the effects of residual products of 2,4-D, 2,4,5-T and similar compounds, the agencies nevertheless restricted the use of these herbicides in the United States some years ago. Since that time, efforts have been made to develop herbicides which are biodegradable into harmless residues within a relatively short time after their application.

One such compound, which has been found to be biodegradable, yet which is effective as a herbicide and plant growth regulator when employed at lower rates, is N-phosphonomethylglycine and various salts thereof. The N-phosphonomethylglycine and agriculturally effective salts have been approved for use by the U.S. Government, and, as a consequence, this herbicide has become extremely successful commercially.

The N-phosphonomethylglycine and certain salts are the only effective and approved post-emergence herbicides in the field. The present commercial compound is the isopropylamine salt of N-phosphonomethylglycine and derivatives thereof.

In field use it is normally applied in amounts of from 0.01 to about 20 pounds per acre, preferably from 2 to 6 pounds per acre.

The N-phosphonomethylglycines, and certain soluble salts thereof, can be made in a number of different ways. One such method, as described in U.S. Pat. No. 3,160,632 (Toy et al., Dec. 8, 1964) is to react N-phosphinomethylglycine (glycinemethylenephosphinic acid) with mercuric chloride in a water solvent at reflux temperature, and subsequently separating the reaction products. Other methods include the phosphonomethylation of glycine and the reaction of ethyl glycinate with formaldehyde and diethylphosphite. The latter method is described in U.S. Pat. No. 3,799,758 (Franz, Mar. 26, 1974). In addition, there is a whole series of patents, relating to N-phosphonomethylglycines, their salts, and derivatives thereof, described as being useful herbicides and plant growth regulators. Such additional patents relating to the N-phosphonomethylglycines, methods of application, methods of preparation, salts, and derivatives, include U.S. Pat. Nos. 3,868,407, 4,197,254, and 4,199,354, among others.

Because of the importance of N-phosphonomethylglycine and certain salts as a herbicide, other methods of making the compounds are constantly being sought in order to provide improved and alternate methods of manufacture.

The instant invention is thus concerned with a novel method for the preparation of N-phosphonomethylglycine.

SUMMARY OF THE INVENTION

It has now been discovered that N-phosphonomethylglycine can be produced in accordance with the following process, which comprises:

(1) reacting N-(diethylphosphonylmethyl)iminobisethanol with an alkali metal hydroxide selected from sodium hydroxide or potassium hydroxide in the presence of water as solvent and a catalytic amount of cadmium oxide or zinc oxide as catalyst under an oxygen free atmosphere and conditions of high temperature and pressure to form N-phosphonomethylglycine tri-salt as an intermediate product, and (2) acidifying said intermediate product.

The N-(diethylphosphonomethyl)iminobisethanol starting compound is a commercial product sold by the Stauffer Chemical Company under the trade name Fyrol ® 6 and is normally used as a fire retardant.

Sodium hydroxide is the preferred alkali metal hydroxide for use in the process of the invention. Potassium hydroxide can also be used, however.

The alkali metal hydroxide is preferably used in excess, and the mole ratio of starting compound to alkali metal hydroxide can range from about 4:6, more preferably from about 4:5.

Suitable acidifying agents for use in step (2) of the reaction include hydrochloric acid, sulfuric acid and the like.

Suitable catalysts include cadmium oxide or zinc oxide, zinc oxide being preferred. By the term "catalytic amount" is meant that minimum amount which is sufficient to catalyze the reaction.

Water is an essential solvent. Water can be added separately, or as a solution of the alkali metal hydroxide. That is, the alkali metal hydroxide can be added as a 50% water solution.

It is essential that this reaction be carried out at high pressure, the most preferred pressure ranging from about 800 to 1500 psi.

It is also essential that the reaction be carried out at an elevated temperature, with the most preferred range being from about 270° to about 280° C.

The reaction described herein may be called a fusion of iminobisethanol with alkali metal hydroxide to form the intermediate N-phosphonomethylglycine tri-salt.

This invention will be better understood by reference to the specific example which follows, which serves to illustrate the invention.

EXAMPLE

A quantity of N-(diethylphosphonomethyl)iminobisethanol (25.0 grams, 0.1 mole) and 16.0 g (0.4 mole) sodium hydroxide (50% solution in water) plus 80 milligrams (mg) (0.005 mole) cadmium oxide was mixed and placed in a 350 milliliter (ml) stainless steel autoclave equipped with an air-driven agitator, manufactured by Autoclave Engineers, Erie, Pa. Prior to charging of the reactants, the autoclave was flushed with nitrogen. The reactants under a nitrogen atmosphere were heated to 270°–280° C. and the pressure increased to 1500 psi over a two hour period due to the evolution of hydrogen, steam and other unidentified gases. The reactants were stirred with an air-driven stirrer and the pressure was maintained at 1500 psi for a period of approximately 30 minutes. The reactants were then cooled to room temperature, the gases were vented off, and the residue was acidified with hydrochloric acid to a pH of 2. The reaction solution was stripped under vacuum, yielding a solid product containing N-phosphonomethylglycine 8.4 g (33.1%) and sodium chloride.

The N-phosphonomethylglycine compound which is made in accordance with the method of the invention, in and of itself, has herbicidal and plant growth regulating efficacy. However, because the acid is not in itself very soluble in aqueous solutions, it is preferred to convert the compound to its salt form for inclusion into herbicidal compositions. Salt forms which have been found to have high rates of herbicidal activity and plant growth regulating activity are the trialkylsulfonium salts of N-phosphonomethylglycine, such as are disclosed in U.S. Pat. No. 4,315,765.

It will be appreciated by those skilled in the art that variations in times, temperatures, pressures and the like can be had in the process described without departing from the spirit of the invention and the scope of the claims herein.

What is claimed is:

1. A method for the preparation of N-phosphonomethylglycine which comprises the steps of:
   (1) reacting N-(diethylphosphonomethyl)iminobisethanol in an oxygen free atmosphere with an alkali metal hydroxide selected from the group consisting of sodium hydroxide and potassium hydroxide, in the presence of water as solvent and a catalyst selected from the group consisting of zinc oxide and cadmium oxide at a temperature ranging from about 270° C. to about 280° C. and pressure ranging from about 800 psi to about 1500 psi, for a combination of time, temperature and pressure sufficient for the reaction to go to completion thus forming as an intermediate product N-phosphonomethylglycine trisalt and
   (2) acidifying said intermediate product thus formed.

2. The method of claim 1 in which the alkali metal hydroxide is sodium hydroxide.

3. The method of claim 1 in which the catalyst is zinc oxide.

4. The method of claim 1 in which the alkali metal hydroxide is potassium hydroxide.

5. The method of claim 1 in which the catalyst is cadmium oxide.

6. The method of claim 1 in which the acidifying agent is hydrochloric acid.

* * * * *